United States Patent [19]

Chiu

[11] Patent Number: 5,429,584
[45] Date of Patent: Jul. 4, 1995

[54] CARDIAC ASSIST METHOD AND APPARATUS

[75] Inventor: Ray C. Chiu, Montreal, Canada

[73] Assignee: McGill University, Montreal, Canada

[21] Appl. No.: 50,392

[22] PCT Filed: Nov. 9, 1990

[86] PCT No.: PCT/CA90/00390

§ 371 Date: Aug. 18, 1993

§ 102(e) Date: Aug. 18, 1993

[87] PCT Pub. No.: WO92/08500

PCT Pub. Date: May 29, 1992

[51] Int. Cl.⁶ ............................................. A61M 1/10
[52] U.S. Cl. ..................................................... 600/18
[58] Field of Search ............................... 600/16, 17, 18

[56] References Cited

U.S. PATENT DOCUMENTS

| | | | |
|---|---|---|---|
| 4,192,293 | 3/1980 | Asrican | 128/64 |
| 5,135,467 | 8/1992 | Citron | 600/16 |
| 5,273,518 | 12/1993 | Lee et al. | 600/16 |
| 5,300,113 | 4/1994 | Arpesella et al. | 600/18 |

OTHER PUBLICATIONS

Anstadt et al., *Prolonged Circulatory Support by Direct Mechanical Ventricular Assistance*, vol. XII Trans. Amer. Soc. Artif. Int. Organs. 1966, pp. 72–79.

David B. Skinner, MD, *Experimental and Clinical Evaluations of Mechanical Ventricular Assistance*, The American Journal of Cardilogy, pp. 146–154.

Dewar et al., *Synchronously Stimulated Skeletal Muscle Graft for Myocardial Repair*, The Journal of Thoracid and Cardiovascular Surgery, vol. 87, No. 3, pp. 325–331 Mar. 1984.

Li et al., *A New Implantable Burst Generator for Skeletal Muscle Powered Aortic Counterpulsation*, vol. XXXV Trans. Am. Soc. Artif. Intern. Organs 1989, pp. 405–407 (Reprint. ASAIO Trans. 1989).

Carpenter et al., *Myocardial Substitution With a Stimulated Skeletal Muscle: First Successful Clinical Case*, The Lancet, Jun. 1985, p. 1267.

*Primary Examiner*—William E. Kamm
*Assistant Examiner*—Scott M. Getzow
*Attorney, Agent, or Firm*—Wolf, Greenfield & Sacks

[57] ABSTRACT

A copulsation and counterpulsation cardiac assist device, wherein the copulsation means includes an extra ventricular cup having and expansible envelope for compressing the heart during systole, and the counterpulsation means comprises a peri-aortic jacket including a fluid expansible balloon for compressing a portion of the aorta during diastole. Belows are provided to be activated by the latissimus dorsi muscles respectively for alternating the supply of fluid pressure to the copulsation device and the counterpulsation device. A heart sensor senses the heart rate, and a pulse train device activates each of the muscles in alternate fashion to contract the respective muscles for producing the required alternating fluid pressure flow. A negative pressure booster includes separate flow chambers through which the alternating fluid pressure flows and a reciprocating pump induces negative pressure in the other of the chambers when fluid pressure flows one chamber to enhance withdrawal of the fluid from a respective one of the copulsation device and the counterpulsation device.

6 Claims, 5 Drawing Sheets

CARDIAC ASSIST METHOD AND APPARATUS

TECHNICAL FIELD

The present invention relates to a cardiac assist method and apparatus, and more particularly, to a combined peri-cardiac implant to assist systole and a peri-aortic device to assist diastole.

BACKGROUND ART

Considerable resources have been invested, by way of research time and money, in the study of replacing the heart, when in is diseased or otherwise failing, in order to prolong the productive life of the patient. Much progress has been made in "heart transplants", and less successful attempts have been made in providing a mechanical replacement for the heart. The major disadvantages with both these developments are well known.

More recently, developments have been made to provide a cardiac assister cup attached to the ventricles and to pump and withdraw air from the cup to assist during systole and diastole, the pulses being coordinated with the rhythm of the heart. This was described by Anstadt, G. L. et al, in "Prolonged Circulatory Support by Direct Mechanical Ventricular Assistance", Trans. ASAIO 12:72–79, 1966, and Skinner, D. B., in "Experimental and Clinical Evaluations of Mechanical Ventricular Assistance", The American Journal of Cardiology, 27:146, 1971. U.S. Pat. No. 4,192,293, Asrican, issued Mar. 11, 1980, also describes a cup or rigid sheath with a fluid expansible envelope for compressing the heart during systole.

Recent developments have also been made to utilize a skeletal muscle, which has been transformed to be fatigue resistant, wrapped around the heart in "dynamic cardiomyoplasty", as described in an article by Dewar, M. L. et al, entitled "Synchronously Stimulated Skeletal Muscle Graft for Myocardial Repair: An Experimental Study", Journal of Cardiovascular Surgery, 87:325, 1984, and the first successful case was reported by A. Carpentier et al in an article entitled "Myocardial Substitution with a Stimulated Skeletal Muscle: First Successful Clinical Case", Lancet 8440:1267, 1985. In dynamic cardiomyoplasty, the latissimus dorsi muscle pedicle is wrapped around the heart, and the muscle is stimulated by an implanted battery-operated, electric pulse device in order to contract the muscle in synchrony with cardiac systole.

Circulatory counterpulsation with the intraaortic balloon is a widely accepted form of cardiac assist. Recently, reports of extended support with the balloon pump have confirmed its efficacy in chronic situations. In several cases, patients were supported from weeks to almost a year. Many more patients with end-stage failure could benefit from chronic counterpulsation support. A major limitation is the patient's dependency on an external power source with its risk of infection and restriction in mobility. A totally implantable counterpulsation assist system would offer an important therapeutic option for patients with end-stage heart failure.

Recent advances in technology and skeletal muscle biology now allow for a viable alternative source in cardiac assistance. It has been demonstrated that skeletal muscle can be made fatigueresistant and powerful enough to continuously assist the heart.

A totally implantable muscle-powered counterpulsation device should have many clinical applications. It could be useful for patients with frequent or chronic heart failure but with some remaining. cardiac function, so that they are not candidates for heart transplantation or artificial heart devices. As a bridge to transplantation, such a device has the advantage of not being tethered to an external power source, so that infectious complications are avoided. The development of a new pulse-train (i.e., burst) stimulator that can summate the contraction pattern of a skeletal muscle to make it resemble that of the myocardium and to synchronize it precisely with the selected portion of the cardiac cycle is described in an article by Carlos M. Li et al, entitled "A New Implantable Burst Generator for Skeletal Muscle Powered Aortic Counterpulsation", published in ASAIO Transactions, July–September 1989, Vol. 35, No. 3, p. 405.

After connecting the balloon to the aorta so that it would be compressed by the latissimus dorsi muscle, the burst stimulator could stimulate the latissimus dorsi muscle during diastole to achieve significant diastolic augmentation.

DISCLOSURE OF INVENTION

It is an aim of the present invention to provide a coordinated and combined totally implantable muscle powered peri-cardiac cup copulsation device combined with a totally implantable and peri-aortic balloon pump which is also skeletal muscle powered.

It is a further aim of the present invention to provide an improved heart rate responsive control device for coordinating the cardiac assist copulsation and counterpulsation devices.

It is a further aim of the present invention to provide a cardiac assist apparatus which is totally implanted but external of the blood circulation system.

A construction in accordance with the present invention comprises a copulsation and counterpulsation cardiac assist device wherein the copulsation means includes an extra-ventricular assist means including a fluid expansible envelope for compressing the heart during systole and the counterpulsation means comprises a peri-aortic jacket means including a fluid expansible balloon for compressing a portion of the aorta during diastole. Muscle powered fluid pressure means are provided for supplying alternating fluid pressure to the copulsation means and to the counterpulsation means. Means are provided for sensing the heart rate and means for producing an electric pulse to the selected muscles to contract the respective muscles in response to signals from the means for detecting the heart rate for producing the required alternating fluid pressure flow. Negative pressure booster means includes adjacent separate flow chambers through which the alternating fluid pressures flow, and a reciprocating pump means having at least a pump element in each of the chambers, such that when fluid pressure flows through one chamber, it induces the pump means to provide a negative pressure in the other chamber to enhance withdrawal of the fluid from a respective one of the copulsation means and counterpulsation means.

In a more specific embodiment of the present invention, the negative pressure booster means includes an implantable housing defining a cavity of circular cylindrical outline having a median wall separating the cavity into at least two sealed fluid pressure chambers and a pump impeller having an axis of rotation in the plane of the median wall with an impeller vane extending in each chamber and the impeller vanes being rotatable in unison within the confines of the respective chambers.

In a more specific embodiment of the present invention, the extra-ventricular envelope is in the form of a peri-cardiac cup. The pressurized fluid to the cup could come from a bellows pump provided under the latissimus dorsi muscle so that it can be compressed by the muscle when the muscle is contracted as a result of a stimulus from the burst stimulator during systole. The extra-aortic (peri-aortic) jacket means includes a fluid expandable balloon extending on an exterior wall of the aorta adapted to compress a portion of the aorta, and a bellows pump provided under the other latissimus dorsi muscle so that it can be compressed by the muscle and the muscle is contracted as a result of stimulus from the burst stimulator during diastole.

Advantages of the combination of the cardiac assist system described herein are that a totally implantable system is provided wherein the ventricular cup and the extra-aortic jacket are coordinated to provide the maximum assist to the heart during both systole and diastole and that a negative pressure assist or booster device is provided for evacuating the cup and/or aortic jacket during diastole and systole respectively. As will be recognized, the cardiac assist system is completely isolated from the blood circulation through the aorta and the heart in order to avoid complications from the blood circulation being in contact with synthetic objects.

In another aspect, the invention provides a cardiac assist system comprising copulsation means for compressing a portion of the heart during systole and decompression during diastole; counterpulsation means for compressing a portion of the aorta during diastole and decompression during systole; fluid pressure means coupled to said copulsation means and to said counterpulsation means, for alternately supplying fluid pressure thereto; said fluid pressure means being in fluid pressure communication with at least two selected body muscles; sensor means for sensing the heart and for generating sensing signals; and means responsive to said sensing signals for generating stimulation pulses to said selected muscles.

In still another aspect, the invention provides a method of assisting systole and diastole comprising effecting compression of a portion of the heart during systole and decompression during diastole, by copulsation means; effecting compression of a portion of the aorta during diastole and decompression during systole, by counterpulsation means; alternately supplying fluid pressure to said copulsation and counterpulsation means, said fluid pressure communicating with at least two selected body muscles; sensing the heart and generating a sensing signal; and generating stimulation pulses to said selected muscles.

BRIEF DESCRIPTION OF THE DRAWINGS

Having thus generally described the nature of the invention, reference will now be made to the accompanying drawings, showing by way of illustration, a preferred embodiment thereof, and in which:

FIG. 5a shows the device in the first operative position, and FIG. 5b shows the device in the second operative position.

MODES FOR CARRYING OUT THE INVENTION

Figure 2:
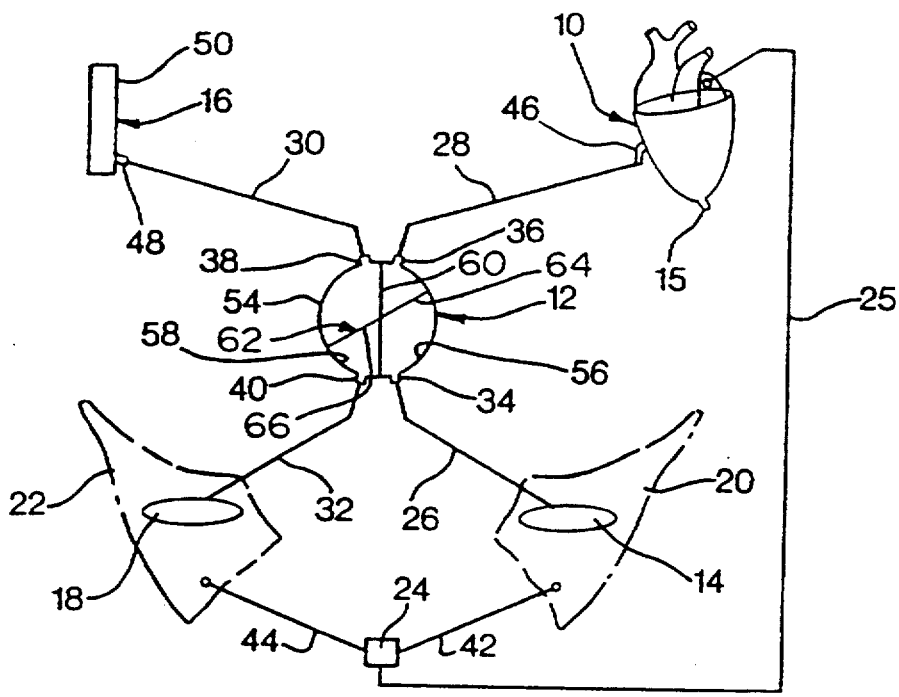
FIG. 2 is a schematic diagram showing the present invention.
Figure 1:
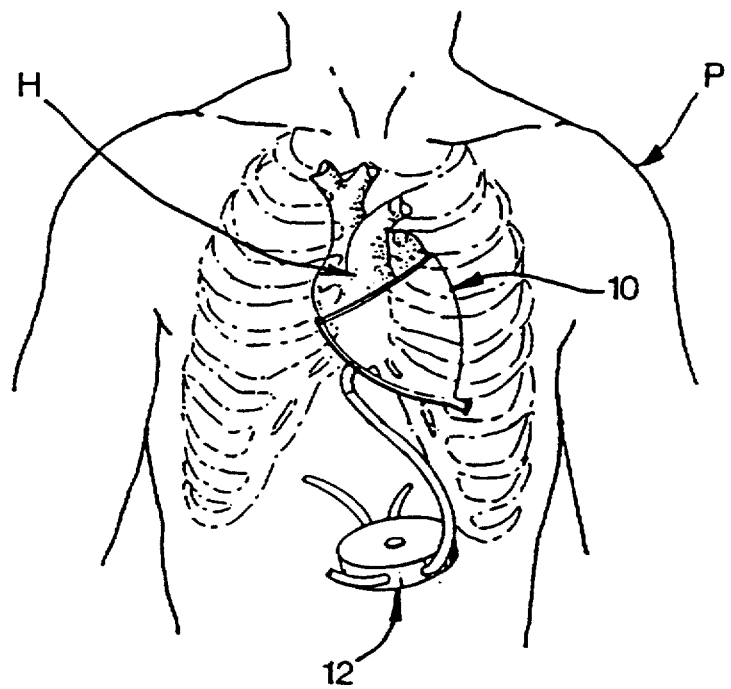
FIG. 1 is a fragmentary perspective view of a portion of the device in accordance with the present invention, situated in relation to the body of a patient.
Figure 3:
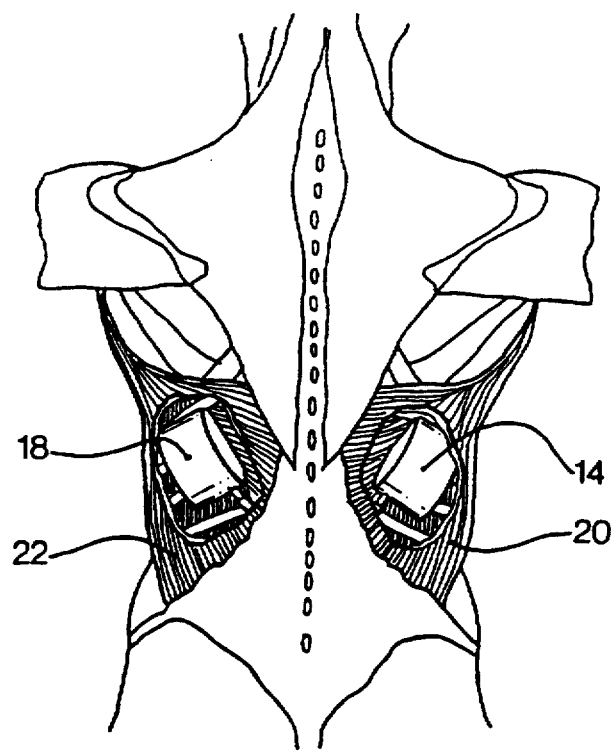
FIG. 3 is a rear view of the patient with muscle layers partly cut away to show the location of details of the present invention.

Referring now to the drawings, there is shown an embodiment of the present invention which includes, for instance in FIGS. 1 and 2, a system comprising in combination the body of a patient P in which a part of the thoracic cage has been illustrated, the heart H, and a ventricle cup 10 placed on the heart. As shown in FIG. 1, a negative pressure booster 12, which will be described further, is located in a natural cavity of the body, e.g., in the abdomen or the chest.

Figure 4A:
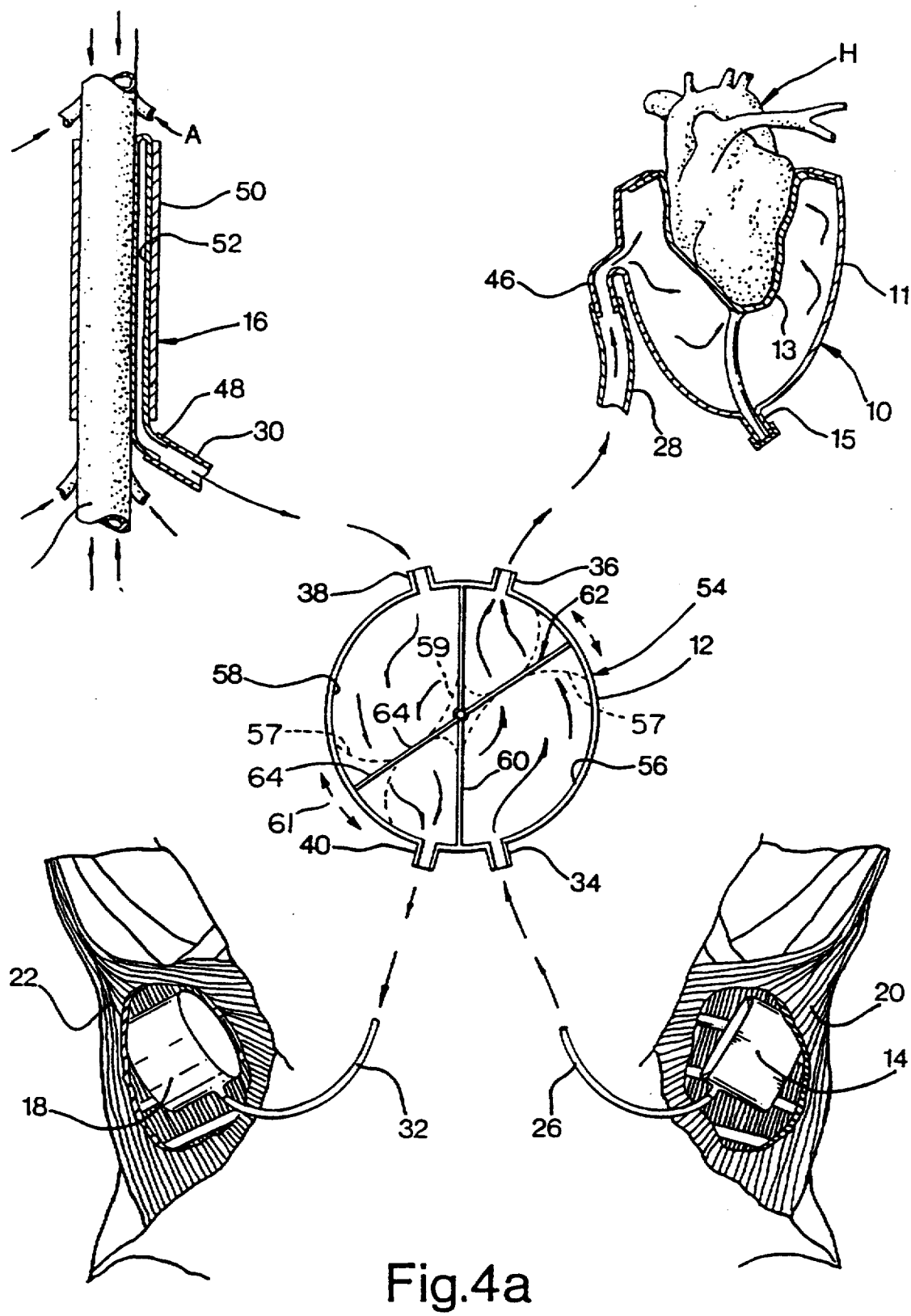
FIGS. 4a and 4b are fragmentary, partly diagrammatic views of details of the present invention, with FIG. 4a showing the device in the first operative position and FIG. 4b showing the device in the second operative position.

Also part of the combination, as shown in FIGS. 2, 4, and 5, is an aortic jacket 16 which communicates with the negative pressure booster 12.

A pair of fluid bellows 14 and 18 are located in association with skeletal muscles, such as the latissimus dorsi muscles 20 and 22 respectively. Finally, a pulse train generator 24 is also located in part of the body with electrical leads to each muscle 20 and 22.

The cup 10 has a construction such as described in the Anstadt article previously referred to and which is herewith incorporated by reference. The Skinner article is also herewith incorporated by reference as describing a typical ventricular cup suitable for use in the present invention. The cup 10 includes a relatively inextensible outer envelope 11 with a liner 13 of flexible stretchable material. The cup 10 is adhered to the heart, preferably by applying a vacuum between the liner 13 and the outer surface of the ventricle by means of tube 15 so that the cup will remain attached to the heart during operation thereof. A flexible fluid conduit 28 extends from the inlet port 46 of the cup 10, to outlet 36 on the negative pressure booster 12.

The negative pressure booster 12 in accordance with the embodiment shown herein is in the form of a circular cylinder housing 54 defining a pair of sealed compartments 56 and 58 divided by a sealed median wall 60. Median wall 60 extends diametrically of the housing 54 and is affixed thereto. An impeller 62, pivotally mounted relative to wall 60, has at least one vane 64 and 66 in each compartment 56 and 58. These vanes 64 and 66 may be sealed by diaphragms 57 between the walls of compartments 56 and 58, and the vanes 62 and 64 respectively, to prevent a mixture of the fluids. Similarly, diaphragms 59 may form a seal between median wall 60 and vanes 64 and 66. Each of the inlet ports 34 and 40 from respective chambers 56 and 58 communicate through conduits 26 and 32 to respective bellows 14 and 18 located underneath respective latissimus dorsi muscles 20 and 22, respectively.

The vanes 64 and 66 may pivotally move relative to the stationary median wall 60, as shown by arrows 61.

Figure 5A:
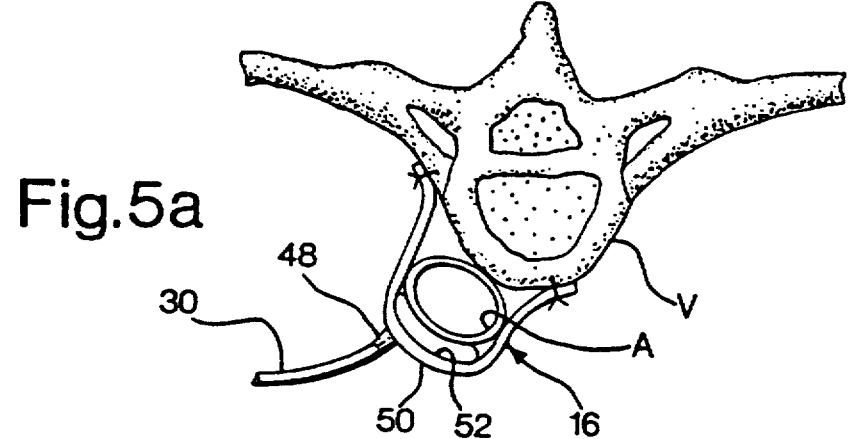
FIGS. 5a and 5b are fragmentary cross-sections of the vertebrae of a person showing the aorta to which a portion of the device in accordance with the present invention has been applied.
Figure 5B:
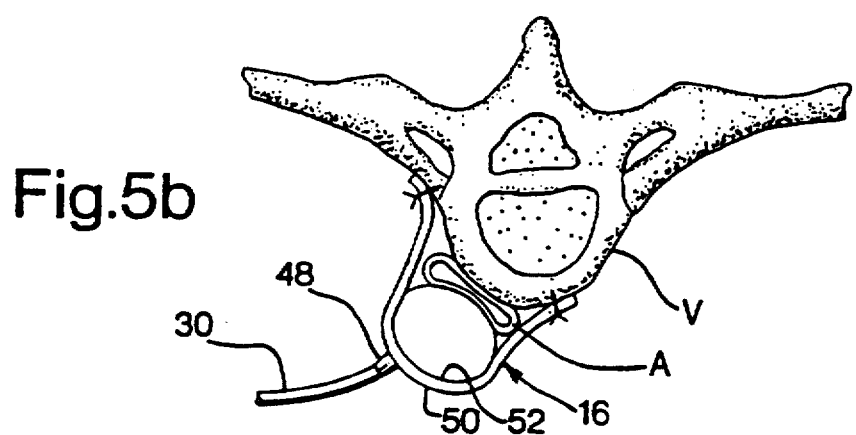

The aortic jacket 16, as shown in FIGS. 4 and 5, includes a relatively rigid outer housing 50, and an elongated balloon 52 which extends between the housing 50 and the aorta A. The aorta A is the descending thoracic aorta, and it is pressed, as in FIGS. 5a and 5b, against the vertebrae V.

The jacket 16 can be stitched or otherwise fastened to the vertebrae as shown in FIGS. 5a and 5b, and the balloon 52 extends between the outer inextensible housing 50 and the aorta A. A flexible tube 30 extends between inlet port 48 on the balloon 52, and the outlet port 38 communicating with chamber 58 in the negative pressure booster 12.

A bellows 18 is provided just under the latissimus dorsi muscle 22 which is placed between the muscle and the ribs. The bellows 18 communicates with the chamber 58 by means of tube 32 extending to inlet 40.

The pulse train generator 24 is of the type having a burst or a series of signals as a pulse train as described in the Li et al article described above. A suitable pulse train generator 24 is available from Medtronic, Inc. The pulse train generator 24 has a computer and is capable of sensing the rate of the heart and includes a sensor lead 25. As the rhythm of the heart changes, the sensor within the computer of the pulse train generator 24 will vary the rate of the discharge of the pulses to the respective muscles 20 and 22. A computer chip within the pulse train generator 24 can be modified or reprogrammed by telemetry. There are leads 42 and 44 to each muscle 20 and 22 respectively for providing the necessary muscle stimulant in order to contract these muscles upon demand.

In the embodiment in accordance with the present invention, the combination was filled with a hydraulic liquid. On the ventricular cup section, 60 cc. of liquid were provided while on the aorta side, 44 cc. were provided. Provision is also contemplated to leave a small plastic nipple (not shown) connected to the conduits in order to top up the system. This nipple could be of the type to receive a hypodermic needle. The capacity of the negative pressure booster 12 is no greater than 200 ml.

Figure 4B:
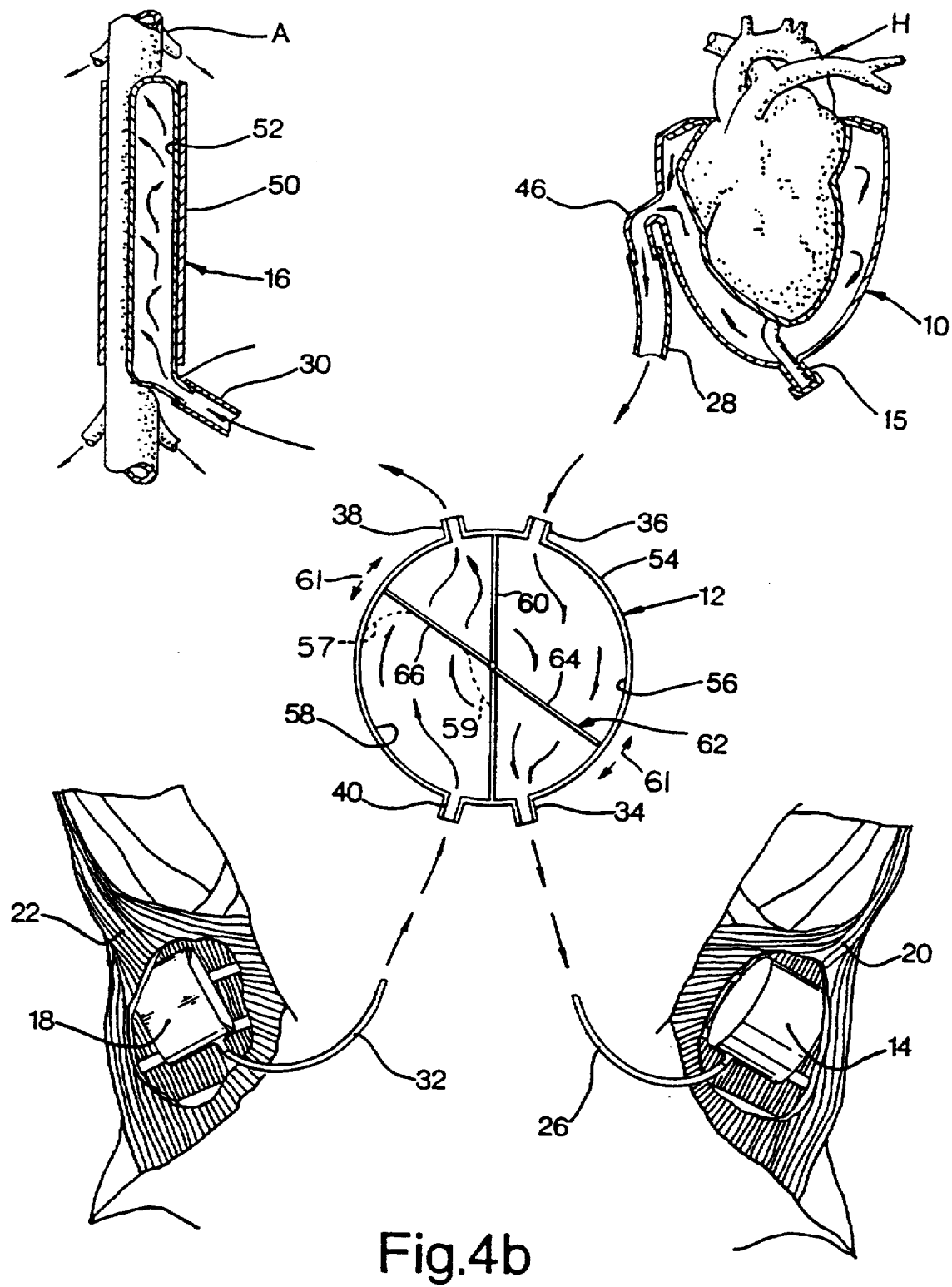

In operation, the heart H is sensed by the pulse train generator 24, and when the heart s about to start a cycle at systole, the pulse train generator 24 will selectively send a signal through the lead 42 to the latissimus dorsi muscle 20 so that it can contract and compress the bellows 14. The fluid from the bellows 14 then travels through the tube 26 to the compartment 56 in the negative pressure booster 12. If the vane 64 is sealed with the diaphragm 57 within the compartment 56, the fluid on the other side of the vane 64 will be forced through the outlet 36, tube 28, through the cup 10 by means of the inlet port 46 to expand the envelope and thus press the liner 13 against the ventricle and assist the heart by compressing it during systole. Immediately thereafter, the latissimus dorsi muscle 20 relaxes, allowing the bellows 14 to expand as the pressure is released from the cup 10 and at the same time a signal is provided from the pulse train generator 24 to the latissimus dorsi muscle 22, thereby contracting the bellows 18 and forcing the fluid out of the bellows 18 through the tube 32 into compartment 58. As shown in FIG. 4b, as the fluid flow passes through the compartment 58, it causes the vane 66 to rotate or pivot clockwise, pressing the fluid out of the housing 54 through the outlet port 38. At the same time, the vane 64 is caused to rotate or pivot clockwise, thus drawing the fluid from the tube 28 and thus the cup 10. Fluid is forced to expand the bellows 20. The cycle is repeated. Thus, every time a latissimus dorsi muscle 20 or 22 is contracted, the other of the muscle 20 or 22 is allowed to relax, and at the same time, the vanes 64 and 66 of the impeller are meant to rotate in the opposite direction to influence the negative pressure on the side which is relaxing.

During systole, the aorta is allowed to relax. However, during diastole, fluid pressure is passed through the tube 30 to the balloon 52 to expand it. The expansion must be towards the aorta because there is no leeway on the jacket side, thus squeezing the aorta and forcing the blood in the aorta towards the heart during diastole.

When the cycle is reversed, of course, fluid pressure again goes to the cup 10 surrounding the heart H to assist systole, and the balloon 52 is allowed to collapse by the fluid being entrained back to the compartment 58 by way of the vane 66. The latissimus dorsi muscles 20 and 22 are, by means of the pulse train generator, caused to operate alternatively between contraction and thus compression against the respective bellows and relaxation.

Figure 6A:
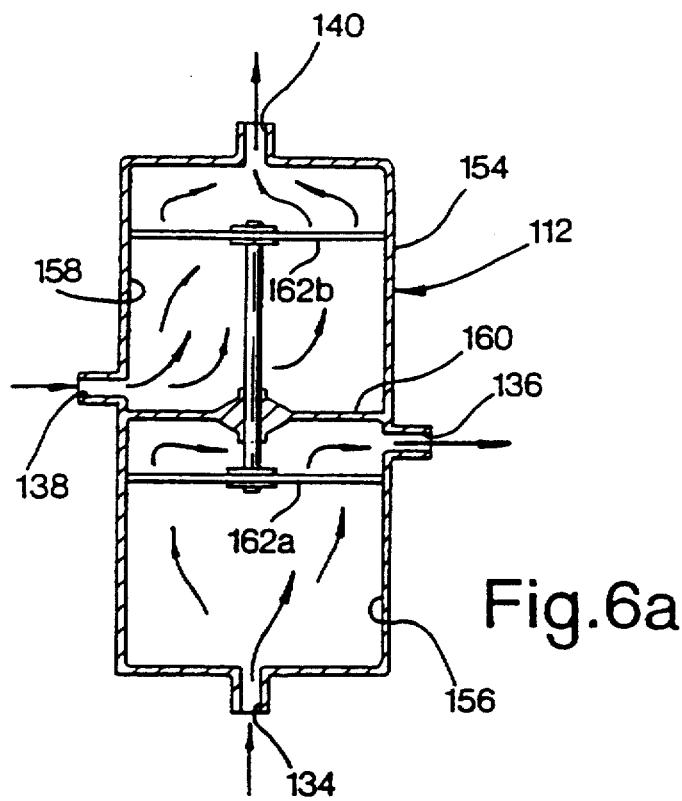
FIGS. 6a and 6b are fragmentary, axial, cross-sectional views of another embodiment of a detail of the present invention.
Figure 6B:
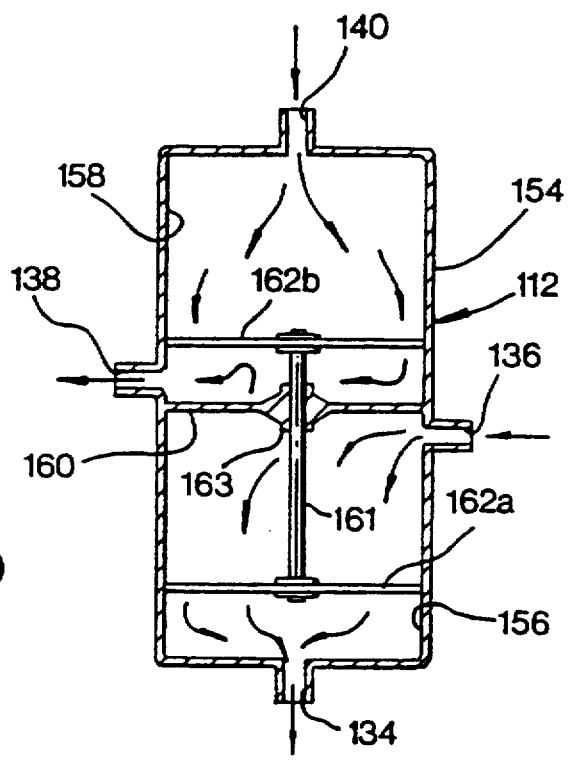

In a further embodiment of the negative pressure booster, there is shown in FIGS. 6a and 6b a negative pressure booster 112 in the form of a piston and cylinder. Like numbers shown in FIGS. 6a and 6b, which compare to the elements in FIGS. 4a and 4b, have been raised by 100. Thus, there is provided a housing 154 defining a chamber in the form of an elongated cylinder having a longitudinal axis and a median wall 160 dividing the chamber into compartments 156 and 158. A sliding piston rod 161 is adapted to slide through a sealed bushing 163 in the median wall 160, and piston-like plates 162a and 162b are on each end of the rod 161 in the respective compartments 156 and 158. Outlet 134 communicates with the bellows 14 while outlet 140 communicates with the bellows 18.

Thus, as shown in FIG. 6a, when the bellows 14 is activated by the latissimus dorsi muscle 20, fluid enters through the outlet 134 into the chamber 156, pressing against the piston plate 162a and thus moving the rod 161 and piston plate 162 in the upward direction. This forces the fluid which communicates with the outlet 136 to flow under pressure towards the cup 10 to inflate it. At the same time, the movement of the piston plate 162b draws the fluid from the aortic jacket 16 to the chamber 158. When the bellows 18 is activated, the reverse occurs, and fluid under pressure enters through the outlet 140 into the chamber 158 to move the pistons 162a and 162b, as shown in FIG. 6b, and reversing the fluid flow previously described.

The invention has been particularly described by reference to the use of the muscles latissimus dorsi. However, other muscles can also be exploited in carrying out the invention, for example, the pectoralis major.

I claim:

1. A copulsation and counterpulsation cardiac assist apparatus comprising copulsation means including a peri-cardiac assist means including a fluid expansible envelope for compressing the heart during systole and counterpulsation means comprising a peri-aortic jacket means including a fluid expansible balloon for compressing a portion of the aorta during diastole, muscle powered fluid pressure means provided for supplying alternating fluid pressure to the copulsation means and to the counterpulsation means, means provided for sensing the heart rate and means for producing a stimulating pulse to selected muscles to contract such muscles in response to signals from the means for producing the required alternating fluid pressure flow, negative pressure booster means including adjacent separate flow chambers through which the alternating fluid pressures flow, and a reciprocating pump means having at least a pump element in each of the chambers such that when the fluid pressure flows through one chamber, it induces a pump means to provide a negative pressure in the other chamber to enhance withdrawal of the fluid from a respective one of the copulsation means and counterpulsation means.

2. An apparatus as defined in claim 1, wherein the negative pressure booster means includes an implantable housing defining a cavity of circular cylindrical outline having a median wall separating the cavity into at least two sealed fluid pressure chambers and a pump impeller having an axis of rotation in the plane o the median wall with an impeller vane extending in each chamber and the impeller vanes being rotatable in unison within the confines of the respective chambers.

3. An apparatus as defined in claim 1, wherein the fluid expansible envelope is in the form of a peri-cardiac cup, and a bellows pump is provided under the latissimus dorsi muscle so that it can be compressed by the muscle when the muscle is contracted as a result of a stimulus from said means for providing a stimulating pulse, and the extra-aortic jacket means includes a fluid expandable balloon adapted for extending on an exterior wall of the aorta adapted to compress a portion of the aorta, and a bellows pump is provided under the other latissimus dorsi muscle so that it can be compressed by the muscle when the muscle is contracted as a result of stimulus from the means for providing a stimulating pulse, during diastole.

4. An apparatus as defined in claim 1, wherein the negative pressure booster means includes an implantable housing defining a chamber, the housing including a median wall separating the chamber into two sealed fluid pressure compartments, a piston rod having a piston on each end thereof, one in each compartment, the rod sliding axially through the median wall, and outlets provided in each compartment of the chamber on either side of the respective pistons in order to provide reciprocal flow of the fluid between the aortic jacket means and the fluid expansible envelope.

5. A cardiac assist system comprising:
   copulsation means for compressing a portion of the heart during systole and decompression during diastole;
   counterpulsation means for compressing a portion of the aorta during diastole and decompression during systole;
   fluid pressure means coupled to said copulsation means and to said counterpulsation means, for alternately supplying fluid pressure thereto;
   said fluid pressure means adapted for being in fluid pressure communication with at least two selected body muscles;
   sensor means for sensing the heart and for generating sensing signals; and
   means responsive to said sensing signals for generating stimulation pulses to said selected muscles.

6. A method of assisting systole and diastole comprising:
   effecting compression of a portion of the heart during systole and decompression during diastole, by copulsation means;
   effecting compression of a portion of the aorta during diastole and decompression during systole, by counterpulsation means;
   alternately supplying fluid pressure to said copulsation and counterpulsation means, said fluid pressure communicating with at least two selected body muscles;
   sensing the heart and generating a sensing signal; and
   generating stimulation pulses to said selected muscles.

* * * * *